US005498237A

United States Patent [19]
Keller

[11] Patent Number: 5,498,237
[45] Date of Patent: Mar. 12, 1996

[54] SQUEEZE-ACTUATED MEDICINAL FLUID APPLICATOR

[76] Inventor: Richard D. Keller, 6416 -Fourth Ave., Takoma Park, Md. 20912

[21] Appl. No.: 381,565

[22] Filed: Jan. 31, 1995

[51] Int. Cl.⁶ .................................................. A61M 5/178
[52] U.S. Cl. .......................... 604/438; 604/223; 604/232; 222/327
[58] Field of Search ................................. 604/38, 223, 227, 604/228, 232; 222/326–327

[56] References Cited

U.S. PATENT DOCUMENTS

| | | | |
|---|---|---|---|
| 2,735,431 | 2/1956 | Swanson | 604/223 |
| 2,773,500 | 12/1956 | Young | 604/223 |
| 3,051,172 | 8/1962 | Bruchhaus | 604/223 |
| 4,776,840 | 10/1988 | Freitas et al. | 604/38 |
| 5,381,928 | 1/1995 | Lee et al. | 222/327 |

*Primary Examiner*—C. Fred Rosenbaum
*Assistant Examiner*—Perry E. Van Over
*Attorney, Agent, or Firm*—A. R. Eglington

[57] ABSTRACT

A squeeze-activated fluid applicator for human manipulation is provided to express the medicinal contents of rupturable capsules; the devise consisting of a shell-like, elongate member of uniform diameter adapted to receive slidingly at its proximal open end an elongate cylindrical member. A cantilever member is adapted to be pivotally mounted midway of the inner elongate member, with a vertical piston operatively connected to the cantilever proximal end, while a strong upward spring bias is provided on the cantilever distal end. A push rod located axially of the cylindrical member can be hand activated to dislodge a bias-arrest feature on the cantilever and to cause the piston to close into a proximal face capsule chamber of the cylindrical member, compressing and expressing the enclosed contents into an adjacent port.

10 Claims, 3 Drawing Sheets

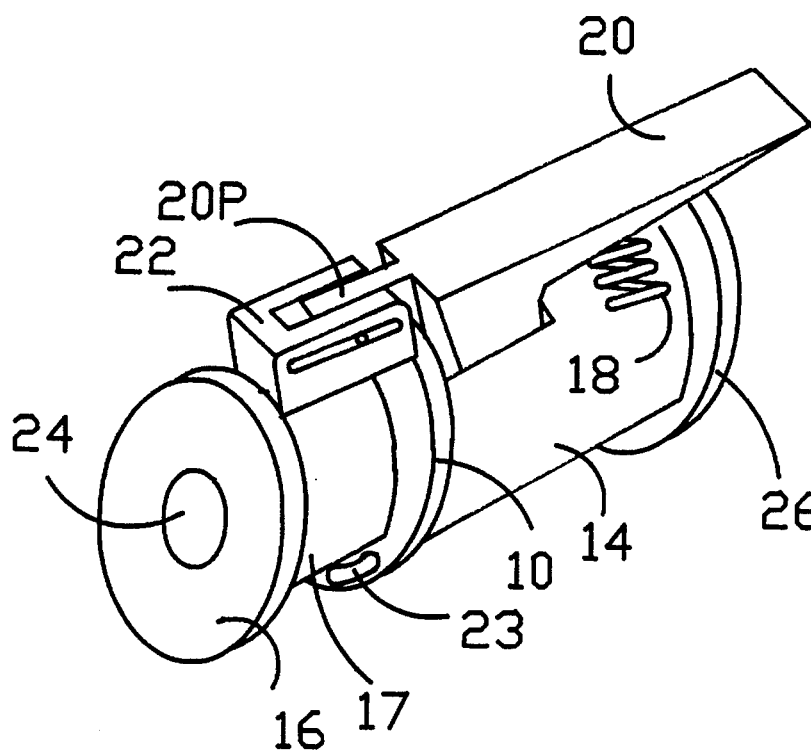
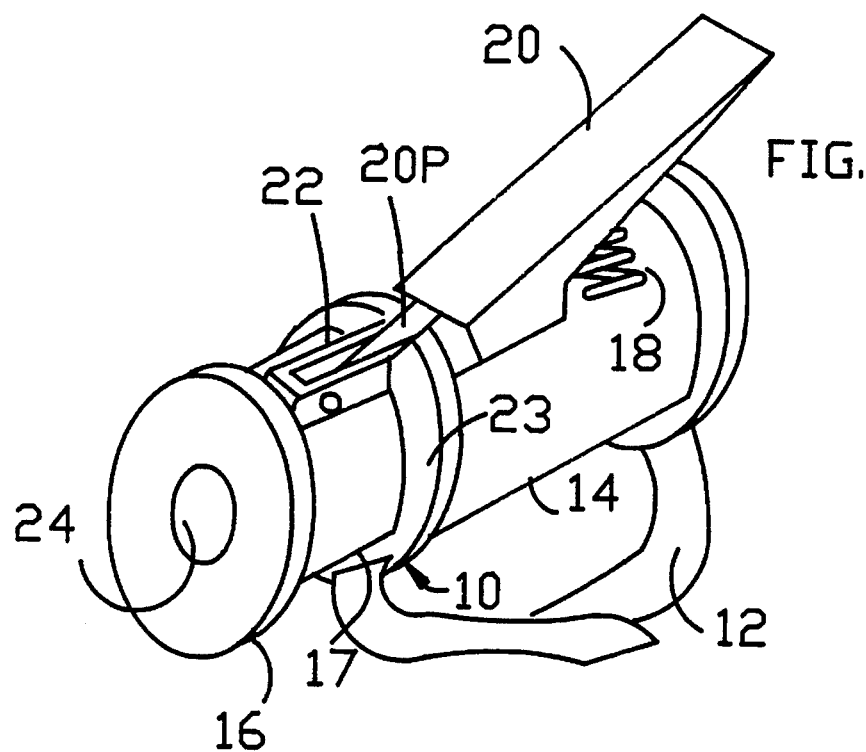

5,498,237

SQUEEZE-ACTUATED MEDICINAL FLUID APPLICATOR

FIELD OF THE INVENTION

This invention relates to a treatment device which may be conveniently manipulated by one hand to effect evacuation of medicament capsules by expressing the contents into patient orifices.

BACKGROUND OF THE INVENTION

Patients who have become invalided by traumatic spinal injuries, or strokes, are sometimes also burdened with a bowel irregularity or flank constipation as a consequence of their impaired elimination function. If the victim is further manually disabled because of spinal nerve damage (paraplegic), or by arthritis leaving only minimal finger mobility, then they would be unable to self-administer relieving medications to their constipated large bowel as needed. A means for compensating for these dual physical infirmities, short of routinely calling for professional treatment, is to be desired and is now to be provided. A treatment device that can be loaded, activated and recycle by those with negligible finger usefulness is much to be desired.

It is therefore a principal object of the invention to provide a device manipulable by those persons without fully effective finger dexterity for the selective expression of medicaments at will into human orifices.

It is another object of the invention to provide a medicament application device configured so as to be cheaply fabricated, yet durable, for manifold reuses. It is yet a further objective to provide one that is handily dosage-loaded discharged and reloaded by patients with only minimal finger dexterity.

It is another object of the invention to provide a liquid medicament infusion system that utilizes a rugged practical structure, requiring only modest manual dexterity and hand strength, so as to effect a release mechanism for the dosage form of medicament intended for administration.

A still further object of the invention is an application device which can be activated, recocked, with the spent capsule discarded and reloaded, all steps being by a patient having only minimal finger mobility and strength.

It is a still further object of the invention to provide for a patient-operated medicament applicator that can be efficiently used by one with only slight manual strength and requires but minimal training.

Accordingly, other objects and advantages as well as a fuller understanding of the invention, may be had by referring to the Summary of the Invention and to the detailed description of the preferred embodiments, in addition to the scope of the invention defined by the claims taken in conjunction with the accompanying drawings.

SUMMARY OF THE INVENTION

The present invention resides in an improved medicinal liquid application device for use with conventional fluid-filled compressable capsules, which can be used to express a premeasured liquid dosage of medication into the orifice of an patient. There is also provided a squeeze-activated fluid expression means adapted for small orifice insertion which comprises: an elongate member with a uniform barrel-like configuration, having an integral bottom wall at one longitudinal end (the distal end), and an open diameter at its other, and functionally proximal, longitudinal end; along with an arcuate aperture provided in the sidewall located nearer the proximal end. Cooperating with the barrel member is an elongate cylindrical member sized to axially and slidingly engage same through the proximal barrel open end. This partly enclosed member having a first chamber located adjacent its proximal ranged longitudinal end, which chamber has one access port coincidental with the outwardly ranged open end of the member, and a second chamber-connecting access port located in the proximal arcuate sidewall periphery of this cylindrical member.

A third operational element is a cantilever member of a length comparable to that of the conjoined barrel member and cylindrical member, which cantilever is centrally and pivotally mounted intermediate the ends of the latter components, conveniently pivotted on the cylindrical member sidewalls.

A depending piston-like member is operatively connected to the proximal longitudinal segment of the cantilever member and controlled with a coiled spring means contacting its opposing distal end, and biasing the distal lever segment outwardly to concurrently bias the proximal end segment inwardly. A depending lug is located on the lever underside intermediate of the member pivot axis and of the lever connection point with the piston means, thus, when engaged, countering the spring-induced bias imposed on the lever proximal end. A second chamber is provided in the cylindrical member intermediate of the first chamber and the cantilever pivot point to accommodate a second lever means pivotally secured within same, which second lever is adapted to provide a detent function to the inwardly biased proximal segment of the cantilever member, while a second coiled spring serves to bias the second lever into the cantilever arrest mode, until exterior forces come into action.

An elongate rod is located in an axial borehole provided in the cylindrical member and it is length-sized to extend between the distal bottom wall of the barrel member and to the proximal aperture of the axial borehole, so as to make non-biasing contact with the second lever body. A coiled third spring is located in the distal open space of the barrel member mounted on the elongate rod, and serving to maintain a separation bias between the barrel bottom wall and the distal, annular-shaped longitudinal end of the enclosed cylindrical member, thus biasing the latter member inwardly of the second chamber. Any compressive pressure exerted on the barrel bottom wall will thrust such rod somewhat more inwardly of the second chamber but sufficiently to dislodge the second lever, pivoting it proximally, lifting clear of the cantilever lug, and permitting the axial bias on the piston member to force same into the first chamber compressing any capulated contents deposited therein.

BRIEF DESCRIPTION OF THE DRAWING

FIG. 1 is a perspective view of a liquid medication insertion device of the present invention with the actuation lever seen in the cocked (medicament recess open) position;

FIG. 2 is another perspective view of the device of FIG. 1 with the activation lever in the uncocked (or sprung) position, (medicament recess confined);

DETAILED DESCRIPTION OF A PREFERRED EMBODIMENT

Figure 3:
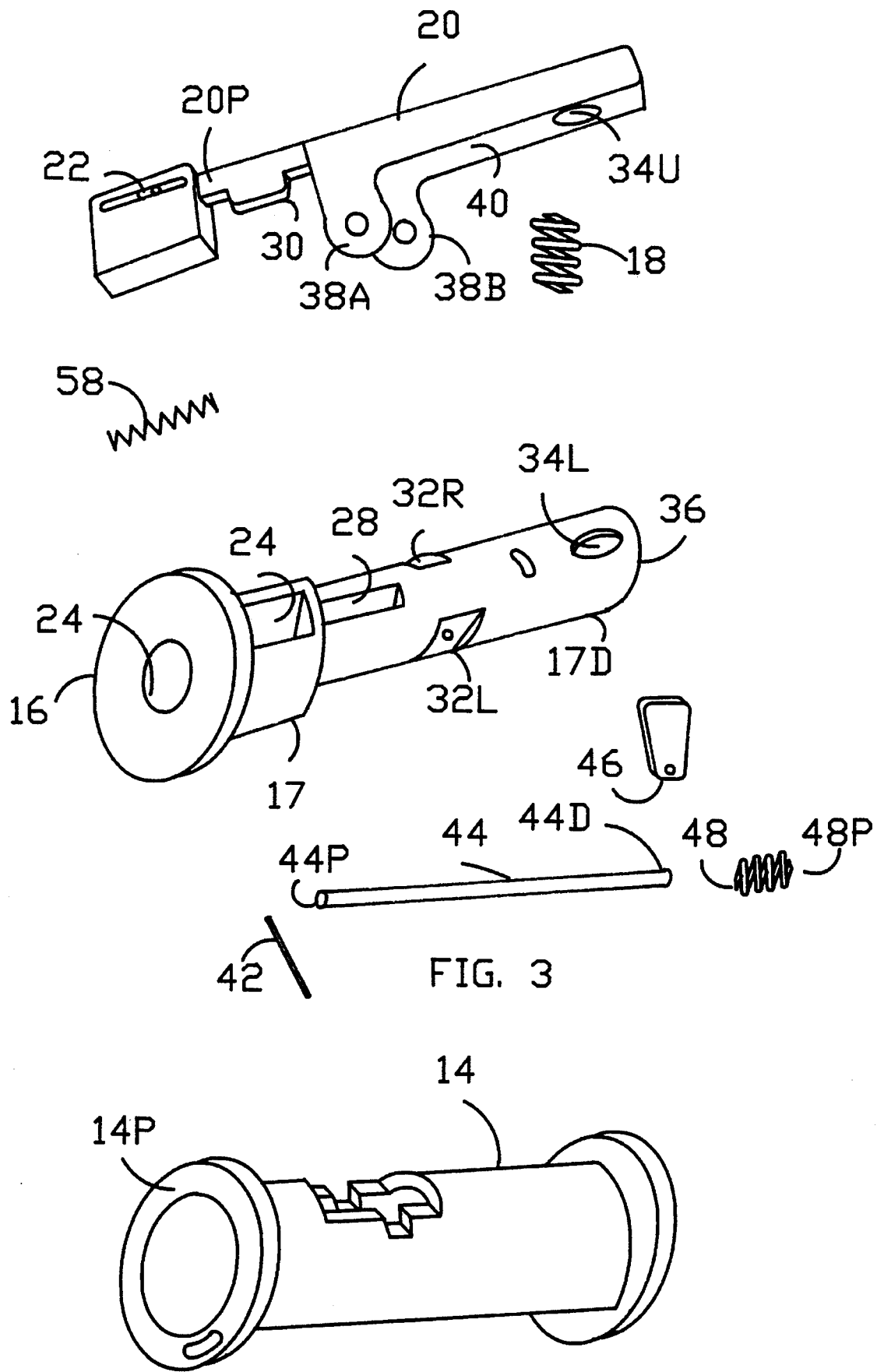
FIG. 3 is an exploded view of the device major components omitting only the medicament capsule to be administered therewith.

Referring now to the drawing, and to FIG. 1 in particular, there is shown an external view of several of the main elements of the assembled device, generally 10 which are: palm of hand retention strap 12; a main cylindrical barrel 14; the operating head 16 of an inner cylindrical member 17; a distal coiled vertical spring 18; and a cantilevered member 20. The proximal end 20P of member 20 is seen in sliding engagement with piston 22. The device is first shown in the cocked posture, which will be better described in relation to the following sectional views. Strap 12 (FIG. 2) is also secured near the distal planar surface of barrel 14 (not seen), and also through the flange 23 on its proximal face.

Flexible strap 12 is adapted to be taken up around the human hand (not seen) while grasping the device 10 circumferentially, and is thus suited to alternately recock same for capsule loading, orifice placement, and the device triggering operation, merely by the exerting of axial compression upon the distal external barrel 26 against the patient orifice.

In the alternate position of FIG. 2 (device sprung, or uncocked), the cantilever member 20 has been released (to be explained) so that vertical spring 18 has pivoted the proximal arm 20P to depress associated piston 22 downwardly into the capsule-holding recess 24, which is located centrally in the ranged proximal head 16 of the inner member 17, concurrently permitting some expansion of distal vertical spring 18.

In the exploded view of FIG. 3, all of the separable but cooperating elements of the operational device are depicted. The full elongate configuration of inner cylindrical member 16/17 is seen, including the outwardly ranged proximal face 16, presenting the capsule holding recess 24, the intermediate cylindrical chamber 28 (with lever out of place) which receives the depending lug 30 of the cantilever member 20; the pair of planar sections 32A & B on the arcuate lateral sides of member 17D; and a circular recess 34L near the member distal end 36, which provides a seating bed for vertical spring 18.

The proxmial end 20P of cantilever member 20 is operatively-connected to proximal end piston 22. Member 20 has depending integral lateral legs 38A & B, for securing same pivotally via pin 42, through planar areas 32A/B. Located intermediate of piston 22 and said support legs is the integral planar surfaced lug 30, which serves in a selective cantilever arrest function, to be described.

Figure 5:
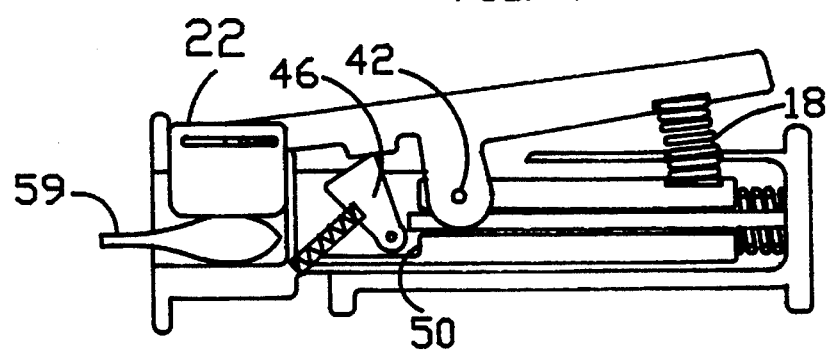
FIG. 5 is a longitudinal sectional view of the same device in the first stage of operation, wherein the ampule is being compressed by a cantilever-driven proximal piston, and its contents are expressing into a patient orifice.
Figure 6:
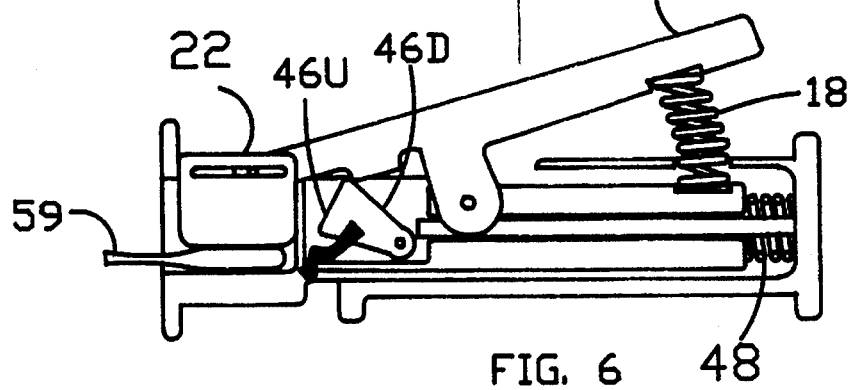
FIG. 6 is another longitudinal sectional view of the device in its final stage of operation wherein the capsule is fully compressed with contents well spent, corresponding to the sprung position of FIG. 2; and, FIG. 7 is an elevational view of the device (corresponding to the view of FIG. 4) after the spent capsule has been removed, wherein the operating lever has been recocked and device is ready for loading of a fresh capsule.
Figure 7:
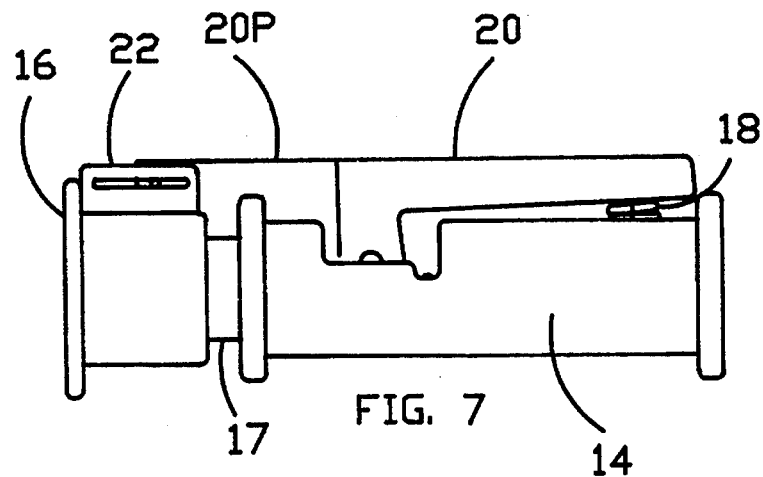

Lastly, the undersurface 40 of the distal end of the cantilever 20 has a circular recess 34U, in a position directly opposing recess 34L on cylindrical member 17. This provides upper and lower anchoring seats for coiled vertical spring 18. Member 42 is a short, elongate metal rod that provides the axial pin for pivotally mounting cantilever 20 on inner member 17D. Disposed axially of inner member 17, and its enclosing barrel member 14, is an elongate rigid rod 44, serving as a push rod for selectively dislodging pivotal internal lever 46. Push rod 44 is normally disposed in a central axial borehole (FIG. 4, et seq) of inner member 17, with its distal rod end 44D carrying somewhat smaller coiled spring 48. This spring is sized to have its proximal end 48P contact the periphery of the distal, annular-shaped surface 36 of inner member 17, while its proximal longitudinal end 48D is retained against the bottom wall (FIG. 4) of the barrel member 14. The thusly interposed spring 48 provides a proximally-directed, forward bias for inner member 17, such that the opposing distal surfaces of inner member 17 and barrel member 14, are maintained in a variable-length, spaced apart juxtaposition, as seen in FIG. 4–6.

Figure 4:
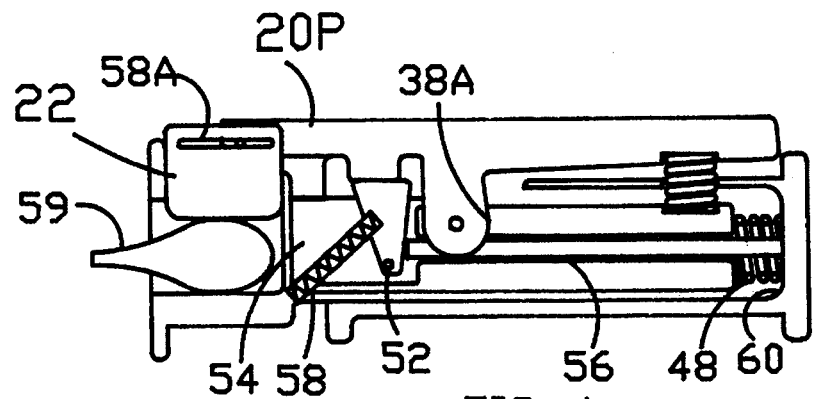
FIG. 4 is a longitudinal vertical section view of the assembled device in the cocked position (corresponding to the perspective view of FIG. 1), including an inserted compressible capsule for medication, that has been positioned for contents expression into a patient orifice.

Averting to sectional view of FIG. 4, there will be there depicted more fully the normally concealed, operational elements of the medication expression device 10. End spring 48 biases inner member 17 leftwardly, so that its intermediate annular surface 50 is normally adjacent to the distal planar surface 46D of inner lever 46. The pivot pin 52 of lever 46 is mounted transversely of intermediate chamber 54 below axial passage 56. A separate, deformable, coiled spring 58 straddles diagonally the chamber 54, and is thus biased so as to normally retain inner lever 46 in the upright position (see FIG. 4). In this lever vertical position, the uppermost planar surface 46U of lever 46 provides an arrest function for cantilever member 20, such that it resists the strong downward bias of the distal coiled vertical spring 18. It thus precludes piston 22 from being deflected downwardly into the proximal recess 24 holding a compressible capsule 59, until desired.

The at rest, or cocked, position of the device is as depicted in FIG. 4. Such will remain static until it is manipulated for dosage expression into a patient cavity. Piston 22 is provided with an elongate horizontal slot 58A/B located below its upper surface in each lateral face, which permits the sliding of a guide pin 22P along such slot, when the proximal cantilever end 20P is activated to effect its slightly arcuate path of force upon movable piston 22.

In operation, the proximal flanged end 16 of inner member 17 is first positioned against a patient orifice (not shown), with the medicament capsule 59 already in place (after the device has been cocked). Slight manual axial movement of barrel 14 in the proximal direction, will further compress push rod spring 48 upon bottom wall 60, forcing main push rod 44 inwardly, enough to dislodge inner lever 46, thus overcoming its supporting deformable spring 58, which becomes flexed proximally. The arcuate dislodgment of arrest lever 46 permits the cantilever member 20 to pivot its proximal end 20P downward, under the bias of vertical spring 18, driving in associated piston 22, compressing the capsule 62, and thus expressing the contents of the enclosed but now ruptured capsule into the adjacent body orifice (not seen), as is depicted in the sequential views of FIGS. 4 and 5.

When the capsule contents expression is complete, the device is then in the uncocked, or spent, position shown in FIG. 6. Drawing the device 10 away from the orifice (not seen) relaxes rod spring 48. Convenient palm slight squeezing of upwardly projecting end 20D of the cantilever, thus lifts piston 22 enough to facilitate removal of the spent capsule. Upon complete compression of the distal end of the cantilever, such will lift the integral lug 30 enough for inner spring 58 to bias inner lever 46 back into its upright position, whereupon the cantilever 20 is again in the cocked mode. Concurrently, push rod 44 has been shifted axially and distally, withdrawing from chamber 54. The arrest lever 46 is now reset, so that the proximal recess 24 is open for fresh capsule placement, without risk of a piston 22 drop, should the manual palm pressure on the device 10 periphery be removed.

In the preferred embodiment depicted, the device in the cocked position is about 5½" in length (FIG. 4) with the device being telescoped less than ¾" to activate the cantilever action and its capsule expression function.

Major elements are molded or fabricated from available machineable plastic stocks, such as rigid high-density polypropylene, Delrin, or ABS plastic. The rigid rods (axial and push) are cut to appropriate lengths from standard metal rod stock, stainless steel or plastic rod, while the suitable strength coiled springs are selected from the large variety of spring length strengths, and diameters, that are commercially available from the conventional spring-making industry.

The rigid rods may also be fabricated from compression-resistant materials, like engineering plastics. Vertical spring 18 is the largest, and it exerts its most compressive force upon piston 22. End push rod spring 48 is shorter and smaller, requiring enough coiled strength to maintain cylindrical member 17 and outer barrel member 14 axially well spaced-apart when at rest, but readily compressible upon axial pressure. However, its spring bias is readily overcome by exerting manual axial pressure on the barrel member. The deformable inner spring 58 is the smallest, requiring only sufficient coiled strength to maintain inner lever 46 upright while in the cocked position, but it is adapted to yield quickly and to deform when push rod 44 exerts its axial force on the opposing vertical surface 46D of inner lever 46.

I claim:

1. A squeeze-activated, medicinal fluid applicator adapted to receive a compressible ampule and so selectively inject its contents into an adjacent orifice located in a firm body comprising:

a) an elongate member having an essentially uniform diameter and barrel-like configuration with a first and distal longitudinal end having an integral bottom wall and the other proximal longitudinal end being open;

b) a first aperture located nearer the proximal open end sidewalls;

c) an elongate cylindrical member sized to axially and slidingly engage said barrel-like member through said proximal open end;

d) a first chamber located adjacent the proximal surface of said cylindrical member having one access port located in the proximal longitudinal end thereof and having its second connecting access port located in the sidewall periphery thereof;

e) a second separate chamber located intermediate the longitudinal ends of said cylindrical member and having a second access port located in the sidewall periphery thereof and coincidentally aligned with said first chamber;

f) a cantilever member of a length substantially equivalent to that of said two elongate members when assembled, and the assembled barrel member and cylindrical member;

g) a depending piston means operatively connected to the proximal longitudinal segment of said cantilever member and aligned and sized to travel within the second access port into said first chamber of said cylindrical member;

h) a depending integral lug located intermediate of the pivot axis of the cantilever member and of the proximal lever connection point for said piston means;

i) a first biasing means interposed between the distal ends of the opposing cylindrical member and cantilever member adapted to exert an upward force upon the distal cantilever longitudinal end;

j) a first recess on the distal end of said cantilever member adapted to receive one free end of the lever arm biasing means;

k) an elongate rod located in an axial passage provided in said cylindrical member serving as a push rod and length-sized to extend between the bottom wall of the barrel member and an aperture connecting with the intermediate second chamber of the cylindrical member;

l) a second biasing means located in the distal open space within said barrel member, serving to a maintain separation bias between the barrel member bottom wall and the distal annular-shaped end of the enclosed cylindrical member;

m) a lever means pivotally secured within the intermediate second chamber of said cylindrical member and adapted to provide an arrest function to the proximal section of said cantilever member so long as it is in contact with the integral lug element thereof; and n) a third biasing means also disposed in said intermediate chamber and positioned to maintain said lever means in its upward lever arrest mode until an opposing bias imposed upon said lever means from said push rod means, exceeds the inherent lever support bias of said third biasing means and is sufficient to dislodge said second lever means from its arrest position.

2. The medicinal applicator of claim 1 in which the barrel-like elongate member is provided with at least one outwardly flanged longitudinal end to aid orifice alignment.

3. The medicinal applicator of claim 1 in which the first aperture in the barrel-like elongate member extends circumferentially for a substantial arcuate segment sufficient to admit of the depending support means for the cantilever member.

4. The medicinal applicator of claim 1 in which the cantilever member is functionally connected to the inner cylindrical member via the first aperture of the barrel member and is in pivotal attachment to the lateral sidewalls of the cylindrical member.

5. The medicinal applicator of claim 1 in which the depending lug is an integral segment of the cantilever member and projects a planar outer surface into the second chamber of the cylindrical member.

6. The medicinal applicator of claim 1 in which the cylindrical member is provided with a first circular recess in its upper surface near its distal end and an opposing second circular recess is provided in the under surface of the cantilever member, both serving to contain the biasing force of said first biasing means against the cantilever.

7. The medicinal applicator of claim 1 in which both of the first and second biasing means are unbendable coiled springs.

8. The medicinal applicator of claim 1 in which the third biasing means is a resiliently deformable, coiled spring.

9. The medicinal applicator of claim 1 in which the push rod is comprised of a suitable compression resistant, rod-shaped metal.

10. The medicinal applicator of claim 1 in which the push rod is formed from a compression resistant material of fabrication.

* * * * *